United States Patent
Kabakov et al.

(10) Patent No.: US 9,232,929 B2
(45) Date of Patent: Jan. 12, 2016

(54) METHOD AND DEVICE FOR FETAL HEART RATE MONITORING WITH MATERNAL CONTRIBUTION DETECTION

(71) Applicant: General Electric Company, Schenectady, NY (US)

(72) Inventors: Serguei Kabakov, Savage, MD (US); Steven M. Falk, Baltimore, MD (US)

(73) Assignee: General Electric Company, Schenectady, NY (US)

( * ) Notice: Subject to any disclaimer, the term of this patent is extended or adjusted under 35 U.S.C. 154(b) by 142 days.

(21) Appl. No.: 13/800,612

(22) Filed: Mar. 13, 2013

(65) Prior Publication Data

US 2014/0276070 A1  Sep. 18, 2014

(51) Int. Cl.
- *A61B 8/02* (2006.01)
- *A61B 8/08* (2006.01)
- *A61B 8/00* (2006.01)
- *A61B 5/024* (2006.01)
- *A61B 5/0255* (2006.01)
- *A61B 5/00* (2006.01)

(52) U.S. Cl.
CPC ............... *A61B 8/02* (2013.01); *A61B 5/0255* (2013.01); *A61B 5/02411* (2013.01); *A61B 8/0866* (2013.01); *A61B 8/0883* (2013.01); *A61B 8/488* (2013.01); *A61B 8/5269* (2013.01); *A61B 8/54* (2013.01); *A61B 8/543* (2013.01); *A61B 5/7221* (2013.01); *A61B 5/7235* (2013.01); *A61B 8/5276* (2013.01)

(58) Field of Classification Search
CPC ........ A61B 8/02; A61B 8/488; A61B 8/5269; A61B 8/0883; A61B 8/54; A61B 8/543; A61B 8/0866; A61B 8/5276; A61B 5/0255; A61B 5/02411; A61B 5/7221; A61B 5/7235
See application file for complete search history.

(56) References Cited

U.S. PATENT DOCUMENTS

| | | | |
|---|---|---|---|
| 3,989,034 A * | 11/1976 | Hojaiban | 600/511 |
| 4,984,576 A | 1/1991 | Schulenberg et al. | |
| 5,113,706 A | 5/1992 | Pittaro | |
| 6,662,043 B1 | 12/2003 | Shine | |
| 8,617,076 B2 * | 12/2013 | Kabakov et al. | 600/453 |

(Continued)

FOREIGN PATENT DOCUMENTS

| | | |
|---|---|---|
| JP | 2011136164 | 7/2011 |
| WO | 2012017364 A1 | 2/2012 |

OTHER PUBLICATIONS

Search Report and Written Opinion From Corresponding PCT Application No. PCT/US2014/023144 dated Jul. 7, 2014.

*Primary Examiner* — Long V Le
*Assistant Examiner* — Colin T Sakamoto
(74) *Attorney, Agent, or Firm* — Andrus Intellectual Property Law, LLP

(57) ABSTRACT

A method and device for monitoring a fetal heart rate includes a reference fetal heart rate detected across an ultrasound depth zone of sensitivity. The ultrasound depth zone of sensitivity is scanned in overlapping increments of a first depth. An average fetal heart rate detected for each overlapping increment is tested for a coincidence with the reference fetal heart rate. Overlapping increments with the coincidence and a maximized signal quality rate are identified. An ultrasound depth increment of a second depth is selected representing the selected adjacent increments. Fetal heart rate is determined from an ultrasound signal returned from a scan depth of the second depth.

20 Claims, 6 Drawing Sheets

(56) References Cited

U.S. PATENT DOCUMENTS 8,696,578 B2 * 4/2014 Kabakov et al. ............. 600/453
2010/0168596 A1 7/2010 Jaeschke et al.
2011/0172540 A1 7/2011 Jackson
2012/0179046 A1 7/2012 Kabakov et al.

* cited by examiner

US 9,232,929 B2

METHOD AND DEVICE FOR FETAL HEART RATE MONITORING WITH MATERNAL CONTRIBUTION DETECTION

BACKGROUND

The present disclosure is related to the field of fetal monitoring. More specifically, the present disclosure is related to fetal heart rate monitoring with the detection of maternal artifacts.

Current methods to detect fetal heart rate (FHR) using Doppler ultrasound have difficulty when applied to obese patients as the ultrasound scanning depth of the solutions has a limited ultrasound penetration range that, when thickness of abdominal fat is taken into account, does not reach the heart of the fetus. Thus, the heart of a fetus with an obese mother is beyond the typical range of ultrasound sensitivity.

While ultrasound penetration depth can be increased either by increasing a duration of an ultrasound transmit pulse and a duration of a receive window or by increasing the duration of the receive window with a fixed transmit pulse, the increased penetration depth causes a decrease in the signal to noise ratio in the received reflected ultrasound signals. The ultrasound beam is produced in a cone shape and reflects across a wider area of physiological structures the deeper an ultrasound wave penetrates before it is reflected and returned. Therefore, ultrasound fetal heart rate monitors with extended penetration depth create a risk to pick up competing physiological signals of the mother, rather than the heart activity of the fetus. Abdominal ECG has been used to acquire fetal ECG signals in obese patients due to these challenges noted above for Doppler ultrasound FHR monitoring. However, the quality of the fetal heart rate determined using fetal ECG through abdominal ECG is typically lower than the quality of fetal heart rate detection experienced in the clinical setting for non-obese maternal patients using Doppler ultrasound. The abdominal ECG requires that a plurality of electrodes be applied to the patient, such electrodes are at risk of producing poor quality signals if careful skin preparation or maintenance of the electrodes is not considered.

An additional effect of this problem associated with increased Doppler ultrasound depth range is confusion of the maternal heart rate (MHR) for the fetal heart rate. Due to the increased risk of picking up the maternal pulse in the abdominal vessels, the MHR signal may dominate the returned ultrasound signals. This can occur in a case wherein the fetal heart signal is weak or lost due to worsening fetal health or due to movement of the fetal heart beyond the ultrasound beam as a result of maternal or fetal movements. In these instances, when operating at an increased ultrasound depth range, the monitor may mistakenly identify the MHR instead of the FHR. Also, if the MHR is elevated, then the monitoring device may lock on the MHR and erroneously produce a result indicating fetal well-being, when in fact the fetal health may be deteriorating.

One previously proposed solution has been to incorporate an additional independent transducer of MHR. Such independent transducer has exemplarily been a pulse oximetry (SpO$_2$) device incorporated into a tocodynamometer. The addition of a still further technology and transducer adds complexity and cost to systems and such combinations present further challenges due to the operation of competing transducers in the same space. Specifically, SpO$_2$ is known to be sensitive to motion artifact and the tocodynamometer membrane can be a source of such motion artifacts, limiting the quality of the MHR determined by the SpO$_2$ transducer.

BRIEF DISCLOSURE

An exemplary embodiment of a method of monitoring a fetal heart rate includes detecting an average fetal heart rate (FHR) across an ultrasound depth zone of sensitivity as a reference FHR. The ultrasound depth zone of sensitivity is scanned in overlapping increments of a first depth. A signal quality for each overlapping increment is calculated. Adjacent overlapping increments with maximized signal quality are identified. An ultrasound probe is operated across an ultrasound depth increment of a second depth representing the adjacent overlapping increments to produce a returned ultrasound signal. Fetal heart rate is determined from the retuned ultrasound signal.

An exemplary embodiment of a device for monitoring fetal heart rate includes an ultrasound transducer operable to transmit ultrasound pulses over a zone of sensitivity. The ultrasound transducer receives an ultrasound signal of reflected ultrasound pluses according to a timing diagram. A fetal heart rate (FHR) detector is operable to produce an FHR waveform and to calculate the average FHR over the FHR waveform. A heart rate coincidence detector compares the determined average FHR over an individual segment to a reference FHR calculated as the average FHR over the zone of sensitivity and produces a coincidence signal indicating a closeness between the average FHR and the reference FHR and a stability of the FHR waveform. A signal quality detector determines the quality of an individual segment of the ultrasound signal and produces a quality signal. A timing diagram selector receives the coincidence signal and the quality signal and selects adjacent overlapping increments with maximized quality signals and produces an indication of a maternal artifact alarm if the coincidence signals of the selected adjacent overlapping increments indicate no coincidence and produces an indication of a timing diagram for operation of the ultrasound transducer.

An exemplary embodiment of an alternative device for monitoring the heart rate of a fetus includes an ultrasound transducer operable to transmit an ultrasound signal. The ultrasound transducer receives reflected ultrasound signals from a plurality of ultrasound depths across an ultrasound depth zone of sensitivity. A digital logic operates the ultrasound transducer according to a timing diagram to scan the ultrasound depth zone of sensitivity and overlapping increments. A signal quality detector calculates a signal quality for each overlapping increment. A fetal heart rate (FHR) detector calculates an FHR from each of the overlapping increments of a first depth size and calculates an average FHR from the FHR waveform. The timing diagram selector identifies adjacent overlapping increments with maximized signal quality and selects a timing diagram for use by the digital logic. The timing diagram is associated with a combined scanned depth of the identified adjacent overlapping increments. The digital logic operates the ultrasound transducer according to the selected timing diagram and the FHR detector calculates the FHR from the received reflected ultrasound signals produced according to the selected timing diagram.

DETAILED DISCLOSURE

Figure 1:
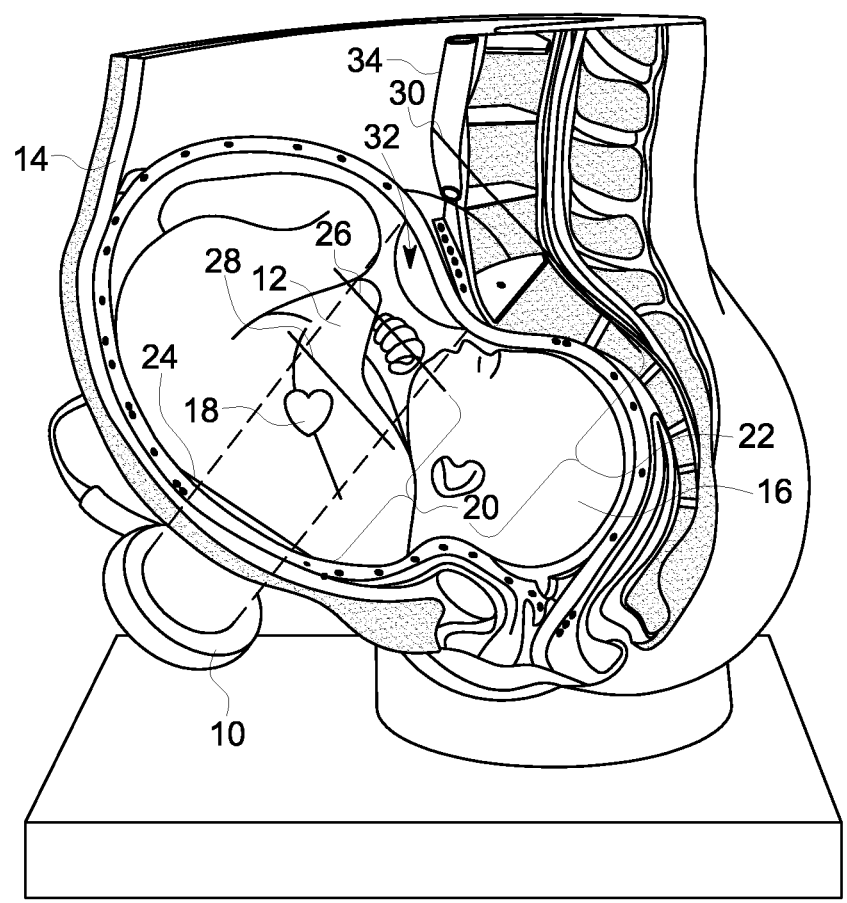
FIG. 1 diagrammatically depicts the use of an exemplary embodiment of an ultrasound transducer on a normal sized patient.

FIG. 1 diagrammatically depicts the operation of an embodiment of an ultrasound transducer 10 to project an ultrasound beam 12 into the body of a maternal patient 14 and a fetus 16. The ultrasound beam 12 is particularly directed at the heart 18 of the fetus 16. FIG. 1 exemplarily depicts a first ultrasound sensitivity zone 20 and a second ultrasound sensitivity zone 22. In the exemplary embodiment depicted in FIG. 1, the first ultrasound sensitivity zone 20 is a near zone and the second ultrasound sensitivity zone 22 is a far zone. It is to be understood that these ultrasound sensitivity zones are merely exemplary and such zones may exemplarily be defined in other manners than that described herein, including a single ultrasound sensitivity zone.

In the exemplary embodiment depicted in FIG. 1, the near zone 20 extends across a depth range between 3 centimeters indicated at 24 to 17 centimeters indicated at 26. In an exemplary embodiment the far zone may extend across a depth range between 14 centimeters indicated at 28 and 28 centimeters indicated at 30. It is to be recognized that these depth ranges are merely exemplary, and in at least one alternative embodiment, the far zone 22 may extend between a depth range of 14 centimeters to other various depths.

As can be seen from FIG. 1, for the maternal patient 14, the near zone 20 encompasses the fetal heart 18, and yet stops short of the placenta 32 and the maternal abdominal aorta 34. Therefore, a fetal heart rate determination made using the near zone 20 of the ultrasound beam 12 under the maternal and fetal conditions depicted in FIG. 1 focus the ultrasound beam 12 on the fetal heart 18, yet the depth of the ultrasound beam zone of sensitivity ends before the placenta 32 and maternal abdominal aorta 34 are scanned, thus eliminating these potential sources of maternal artifacts.

Figure 2:
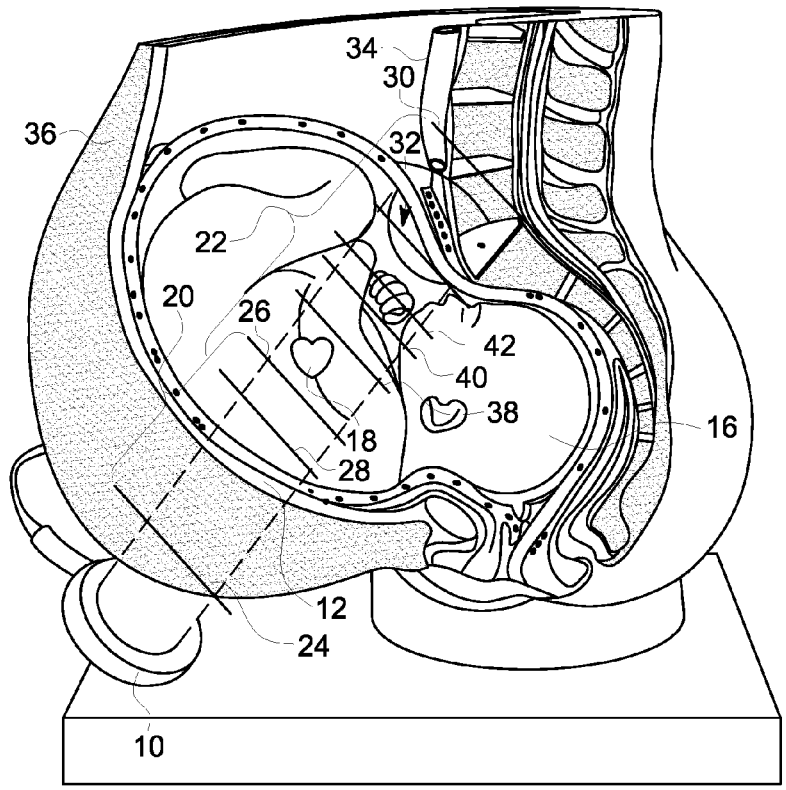
FIG. 2 diagrammatically depicts the use of an exemplary embodiment of the ultrasound transducer on an obese patient.
Figure 3:
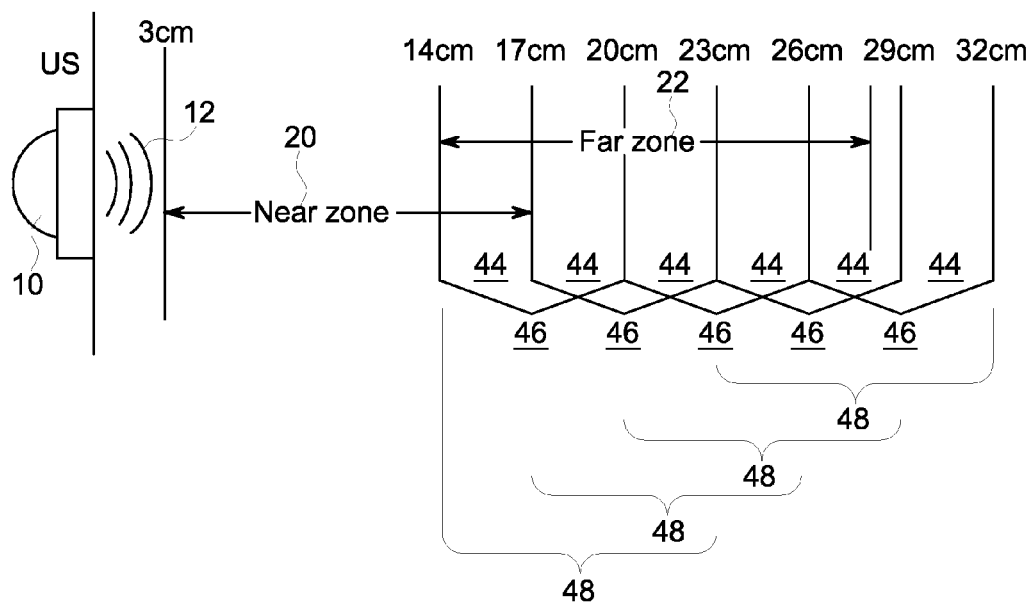
FIG. 3 diagrammatically depicts an exemplary embodiment of an ultrasound transducer zone of sensitivity.

The diagram of FIG. 1 is compared to that of FIG. 2 wherein the same ultrasound transducer 10 is applied to the abdomen of an obese maternal patient 36. As can be seen in FIG. 2, the fetal heart 18 is now at a depth outside of the range of the near zone 20. While the fetal heart 18 is located within the depth range of the far zone 22, the placenta 32 and maternal abdominal aorta 34 are also within this far zone 22. Additional depth indications are provided in FIG. 2, including 20 centimeters at 38, 23 centimeters at 40 and 26 centimeters at 42. FIG. 3 diagrammatically depicts the zones and depth ranges depicted in FIG. 2. In the exemplary embodiment depicted in FIG. 3, ultrasound depth ranges are broken into 3 centimeter depth zones which will herein be referred to as micro zones 44. While the micro zones 44 exemplarily described herein will be of a size of 3 centimeters, it will be recognized that in alternative embodiments other various micro zone sizes including, but not limited to, 1 centimeter, 2 centimeters, or 4 centimeters may be used within the present disclosure. Two adjacent micro zones 44 constitute a mini zone 46 as used in the present disclosure. Thus, in the exemplary embodiment described herein, the mini zone 46 is an ultrasound depth range of 6 centimeters. It is to be noted that adjacent mini zones 46 overlap as adjacent mini zones share a common micro zone 44. Two adjacent mini zones 46 constitute a macro zone 48 as used in the present disclosure. Thus, the macro zone 48 covers three consecutive micro zones 44 and therefore in the exemplary embodiment described herein represent an ultrasound scan range depth of 9 centimeters.

Figure 7:
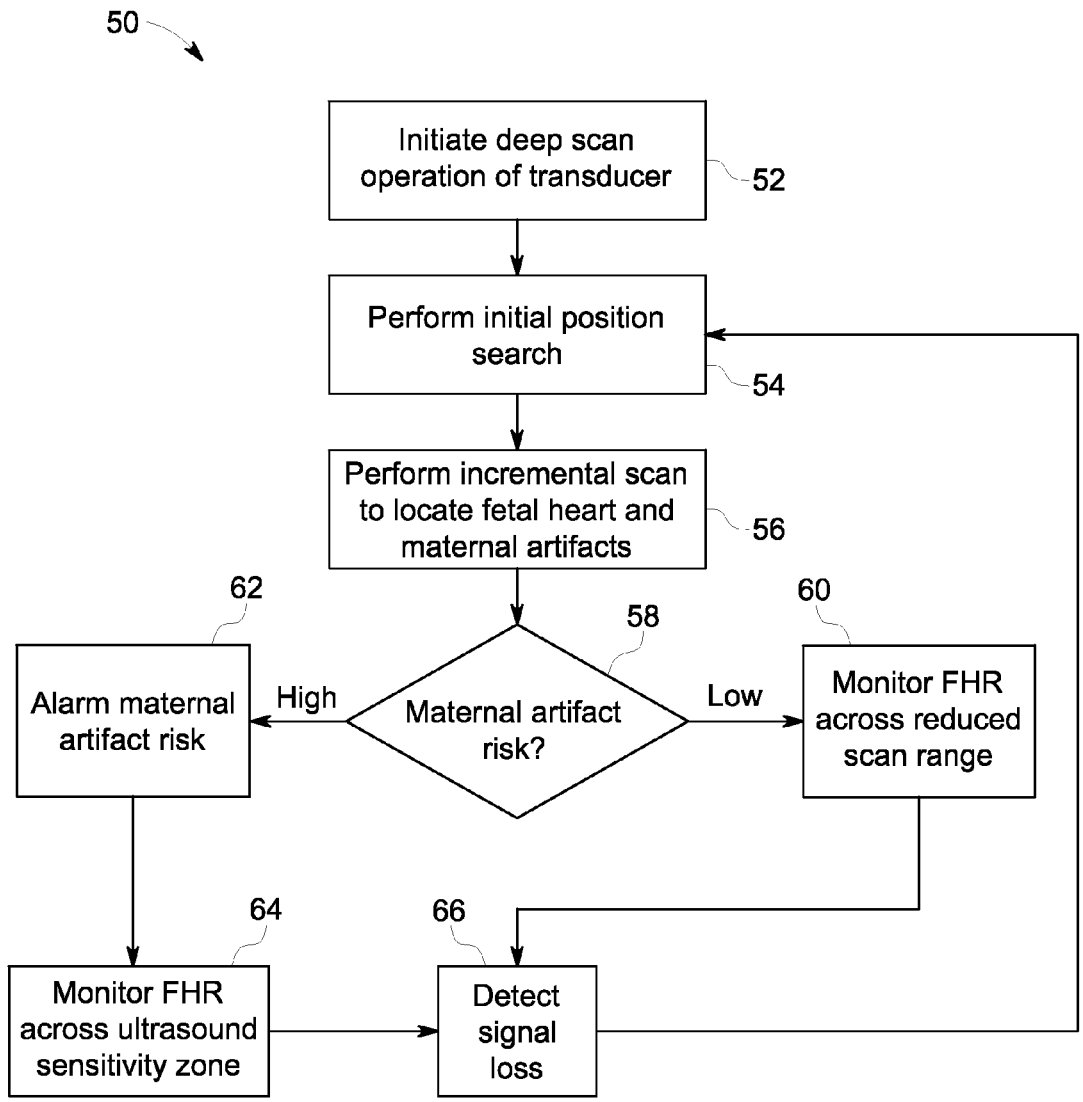
FIG. 7 is a flow chart that depicts an exemplary embodiment of a method of monitoring fetal heart rate.

With reference to FIGS. 3 and 7, FIG. 7 is a flow chart that depicts an exemplary embodiment of a method 50 of monitoring a fetal heart rate. It is to be noted that in embodiments, such method may be used across all depths of ultrasound scanning; however, other embodiments such as the method 50 exemplarily shown in FIG. 7 are applied specifically to deep or far ranged ultrasound scanning, exemplarily shown as the far ultrasound sensitivity zone 22 in FIG. 3. At 52 a deep scan operation of the ultrasound transducer is initiated. This deep scan operation of the ultrasound transducer may include one or both adjusting the ultrasound signal transmission or receiving gating to select for returned ultrasound signals from the selected far ultrasound sensitivity zone. At 54 an initial position search is conducted in which the ultrasound transducer is positioned on the abdomen of the maternal patient and coarsely adjusted such that the ultrasound transducer receives reflected ultrasound signals that include the fetal heart signal.

Next at 56 incremental scans are performed to locate the fetal heart and maternal artifacts, if any, within the far ultrasound sensitivity zone. In embodiments as disclosed in further detail herein, the locating of the fetal heart can include identifying a micro zone depth in which the fetal heart is located. Once the micro zone that includes the fetal heart is identified, maternal artifacts can be searched for in either a macro zone centered on the micro zone that includes the fetal heart, or in an alternative embodiment, a mini zone above and below the identified micro zone can be scanned for maternal artifacts.

At 58 maternal artifact risk is evaluated. Embodiments of the determination of maternal artifact risk are described in greater detail herein. If the maternal artifact risk at 58 is identified as being low, then the fetal heart rate monitor is operated to monitor the fetal heart rate across a reduced scan range within the far ultrasound sensitivity zone. In a non-limiting embodiment, this reduced scan range may be the macro zone centered on the micro zone in which the fetal heart is located. If the maternal artifact risk is identified as being high, then an alarm indication of maternal artifact risk is produced at 62 and fetal heart rate is monitored at 64 across the entire far ultrasound sensitivity zone. Either of the monitoring of fetal heart rate at 62 or 64 are maintained until at 66 a ultrasound signal loss is detected. An ultrasound signal loss may occur if the ultrasound transducer becomes mis-positioned or dislodged, exemplarily through movement of the maternal patient, or the fetus sufficiently moves within the maternal patient such that the ultrasound beam from the ultrasound transducer is no longer directed at the fetal heart. In such an event, the method may return to perform an initial position search at 54 and reevaluate the fetal heart and maternal artifacts.

Figure 4:
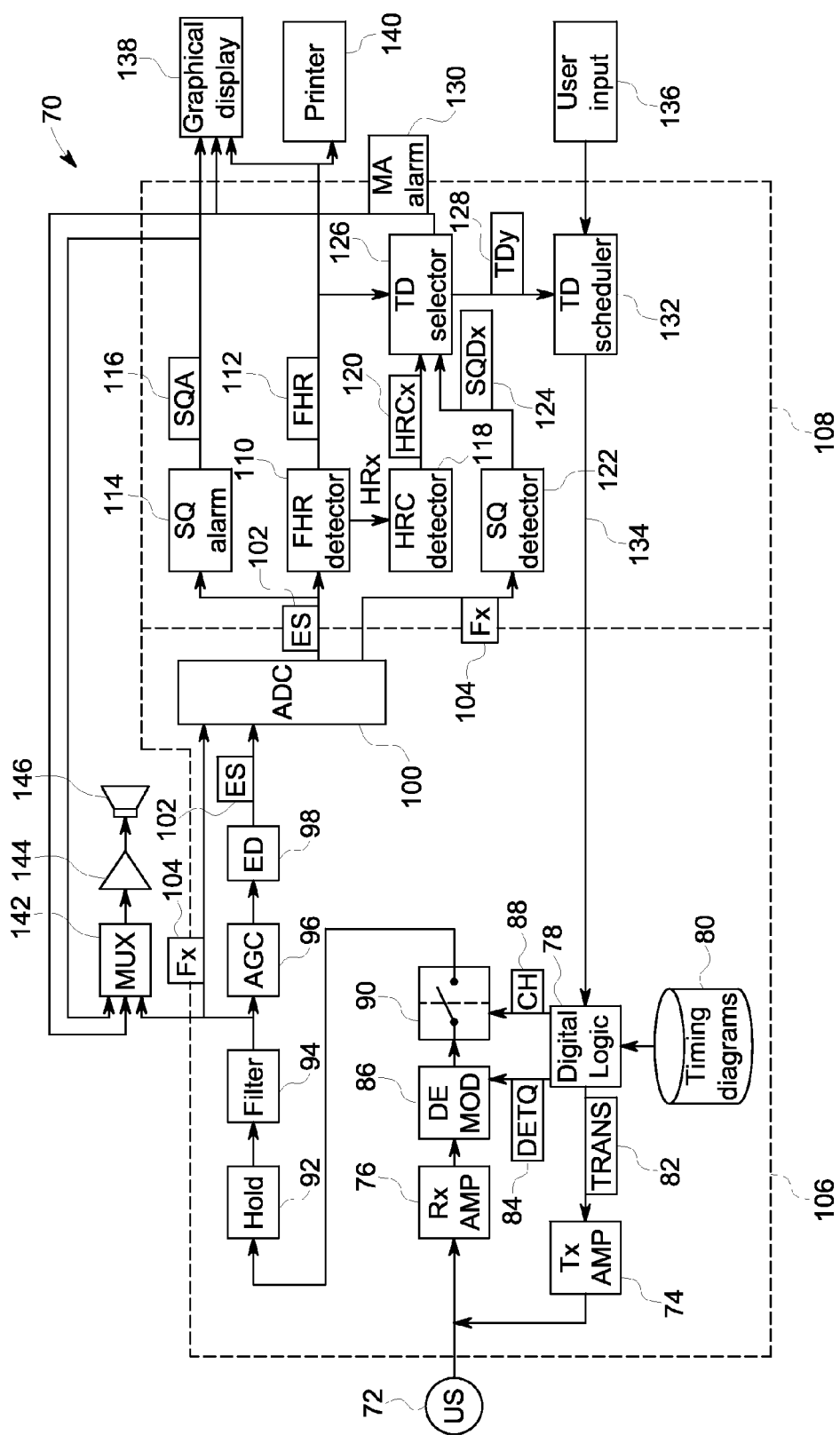
FIG. 4 is a schematic diagram of an exemplary embodiment of a fetal monitoring device.

FIG. 4 is a schematic diagram that depicts an embodiment of a fetal monitoring device 70 such as may exemplarily be used to carry out embodiments of the method as described above with respect to FIG. 7. The fetal monitoring device 70 includes an ultrasound transducer 72 that produces ultrasound signals that are directed into the abdomen of the maternal patient and receives ultrasound signals reflected off of the physiological structures of the maternal patient and fetus. The ultrasound transducer carries out these functions by the operation of a transmission amplifier 74 and a receiving amplifier 76.

The transmission amplifier 74 is connected to digital logic 78 that may exemplarily be an FPGA, a CPLD, or processor. The digital logic 78 executes a timing diagram exemplarily from a computer readable medium 80 storing a plurality of timing diagrams. The timing diagrams each are associated with transmission and receive signals such as to operate the fetal monitoring device 70 to monitor a particular depth or zone within the fetus and maternal patient. The digital logic 78 produces a plurality of transmit tone signals (TRANS) 82 to the transmission amplifier and a plurality of received tone signals (DETQ) 84 to a demodulator 86 such as to only demodulate those ultrasound signals reflected off of the abdominal physiological structures, the reflected signals are associated with the ultrasound depth range or zone defined by the operating timing diagram. The digital logic 78 also provides a received strobe pulse (CH) 88 to a switch 90 to pass the demodulated ultrasound signals from the selected depth range or zone for further signal processing.

Basic signal processing is formed by a hold 92, a filter 94, an automated gain controller (AGC) 96 and an envelope detector 98. The hold 92 may represent a hold stage of a sample on a hold function and may be implemented as a capacitor. The filter 94 is exemplarily a band pass filter with a pass band between 100-300 Hz. The output of such filter being a signal generally representative of the fetal heart component (Fx) 104 of the Doppler signal acquired by the ultrasound transducer 72. The fetal heart component 104 is provided to an analog to digital converter (ADC) 100. An automated gain controller (AGC) 96 processes the fetal heart component before the signal is provided to an envelope detector 98 that produces and envelope signal 102 representative of the heart activity of the fetus. The envelope signal 102 is also provided to the ADC 100. These aforementioned components exemplarily represent a front end 106. The front end 106 may exemplarily be implemented in hardware or other analog implementation. However, it is to be recognized that in alternative embodiments, the ADC 100 may be used in another manner and at least portions of the front end 106 implemented digitally or through software. It is understood that in embodiments analog configured components may receive digital control signals such as exemplarily described with respect to the digital logic 78.

The ADC 100 provides a digitized envelope signal (ES) 102 and a digitized fetal heart component (Fx) 104 to an exemplary back end 108 of the fetal monitoring device 70 wherein the fetal monitoring device back end 108 may be implemented in hardware or software operating on a processor, or a combination of both. In embodiments implemented in whole or in part through the execution of software by a processor, it is exemplarily understood that such processor may be a general or specific use processor that accesses computer readable code sorted on a computer readable medium and upon execution of such computer readable code, the processor carries out the functions of the various components of the back end 108 as described herein.

The digitized envelope signal 102 is provided to an FHR detector 110. The FHR detector 110 is exemplarily an auto correlation-based fetal heart rate detector that processes the envelope signal 102 with an auto correlation algorithm in order to determine a fetal heart rate (FHR) waveform (HRx) 112 from the received envelope signal 102. The digitized envelope signal 102 is also provided to a signal quality alarm 114. The signal quality alarm 114 analyzes the envelope signal 102 to determine that a fetal heart component in fact exists in the envelope signal 102. If no fetal heart component, or too low of quality of fetal heart component is identified, then the signal quality alarm 114 generates a signal quality alarm (SQA) 116. The signal quality alarm 114 may produce a signal quality alarm 116 exemplarily in the event that the fetus moves and the fetal heart is outside of the ultrasound beam projected into the abdomen of the maternal patient or if the maternal patient moves in such a manner such as to disturb or displace the ultrasound transducer such that no fetal heart signal is returned to the ultrasound transducer.

In an embodiment as disclosed in further detail herein, a heart rate coincidence (HRC) detector 118 receives an initial determination of a reference fetal heart rate. The reference fetal heart rate may be determined as an average of a FHR waveform obtained from a scan of an entire ultrasound sensitivity zone. The heart rate coincidence detector compares this reference FHR against the average FHR calculated from each of the FHR waveforms 112 from an ultrasound segment. The result of this comparison is referred to as a coincidence between the reference FHR and each average FHR. In an embodiment, this is output as the heart rate coincidence (HRCx) signal 120.

An exemplary embodiment of an algorithm implemented by the HRC detector 118 may be:
  If ABS (mHRx−mHR1428)<thresh*mHR1428
    then HRCx=1.
  Otherwise HRCx=0.
Where x=scan range intervals representing consecutive mini zones across the ultrasound sensitivity zone. mHR1428=the average heart rate measured across the ultrasound sensitivity zone. An mHRx is the average heart rate at each of the scanned mini zones. In a non-limiting embodiment, 24 heart rate samples are averaged from each mini zone segment where the fetal heart rate output is sampled at a rate of four samples per second and therefore the length of each scan segment at each micro zone scanned depth is 6 seconds. In a non-limiting example, the threshold (thresh) equals 0.05, meaning that a positive coincidence signal indicates that the fetal heart rate calculated from the mini zone is within 5% of the average fetal heart rate calculated across the ultrasound sensitivity zone.

In another embodiment, the HRC detector 118 further determines a stability of the FHR waveform received from the FHR detector 110. In embodiments as disclosed herein, this determination of FIR waveform stability may be incorporated into the HRCx signal 120. As used herein, the stability of the FHR waveform refers to whether or not pen lifts are identified in the FHR waveform. If there are no pen lifts, then the FHR waveform is considered to be stable. If pen lifts are found, then the FHR waveform is considered to be unstable. Thus, an exemplary embodiment of an algorithm implemented by the HRC detector 118 to incorporate stability may be:
  If pen lifts (HRCx)
    then HRCx=0
  Otherwise:
  If ABS (mHRx−mHR1428)<thresh*mRH1428
    then HRCx=1
  Otherwise HRCx=0
wherein HRx=is the exemplary 6 second segment of the FHR waveform for the ultrasound segment.

The fetal heart component (Fx) 104 as obtained from the returned ultrasound signal filtered at the filter 94 and digitized is provided to a signal quality (SQ) detector 122. The SQ detector 122 produces an indication of signal quality (SQDx) 124 that is indicative of the quality of the fetal heart component of a monitored segment, exemplarily a segment of an ultrasound signal at a particular mini zone. The signal quality is exemplarily determined as the energy (or in alternative embodiments power) in the Fx signal 104 received by the SQ detector 122. A non-limiting embodiment of an algorithm implementing the signal quality detection at 122 includes:

$$SQDx = sum(Fx[2*i]*Fx[2*i]), i=1 \ldots I-1$$

Where X is an identification of each of the mini zone segment being evaluated. I=T×FS. FS=1,000 samples/sec which is the exemplary sampling rate of the ADC 100. T=6 seconds which is an exemplary length of the ultrasound signal segment Fx.

The HRCx 120 and SQDx 124 signals are provided to a TD selector 126 that provides the dual functions of determining the presence or heightened risk of a maternal artifact and selects an appropriate timing diagram for monitoring of the fetal heart rate.

Figure 5:
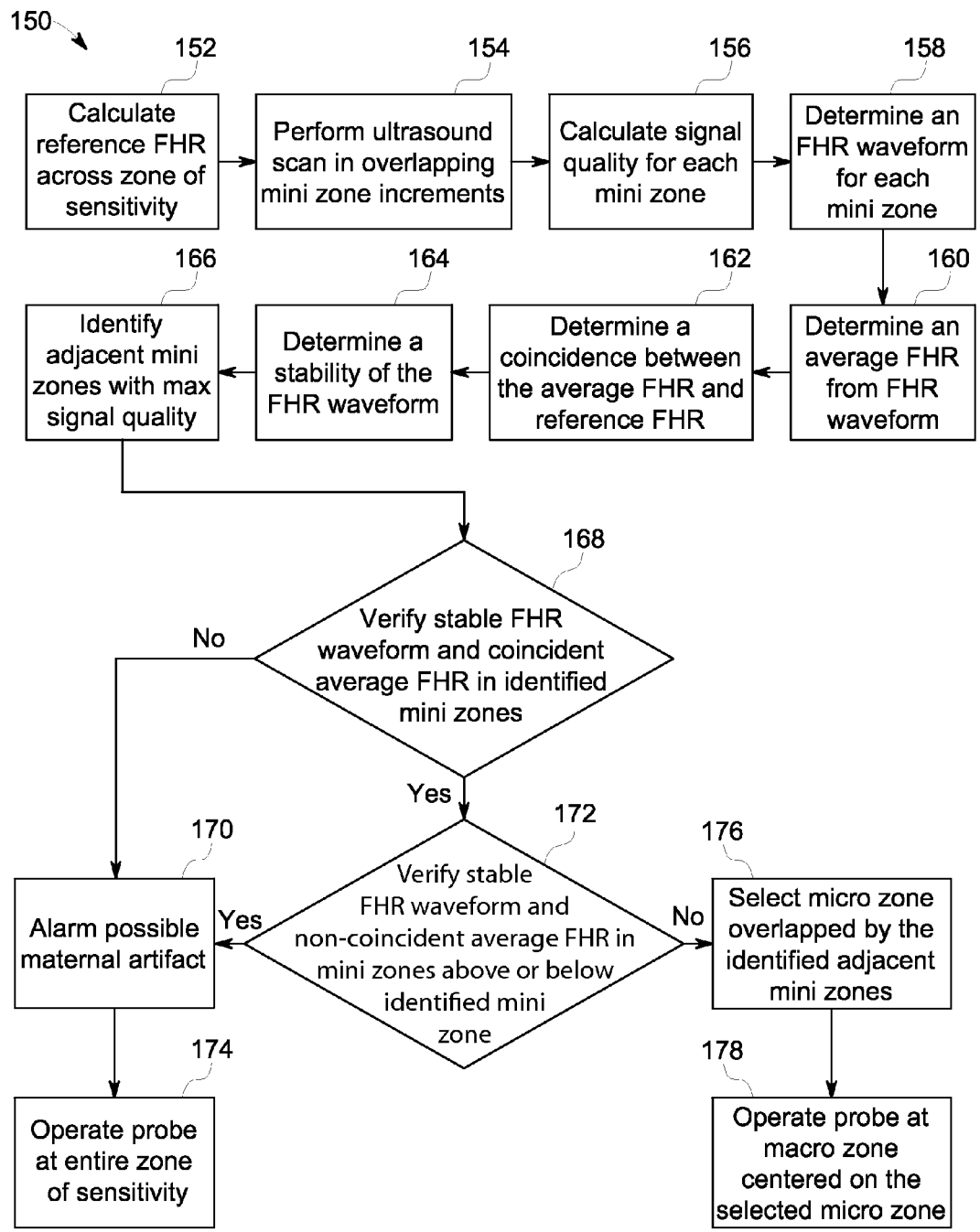
FIG. 5 is a flow chart that depicts an exemplary embodiment of a method of monitoring fetal heart rate.

In an exemplary embodiment, the TD selector 126 performs this analysis according to a method 150 exemplarily presented the flow chart of FIG. 5. It will be noted that in embodiments, portions of the method 150 may also be carried out by other components shown in FIG. 4, including, but not limited to, the FHR detector 110, HRC detector 118, or SQ detector 122. Referring to FIG. 4 and FIG. 5, a reference FHR across the zone of sensitivity is calculated at 152. As described above, the reference FHR can be the average FHR across the zone of sensitivity. Next, the zone of sensitivity is scanned in overlapping mini zone increments at 154 such as in the manner already described above.

Once the mini zones have been scanned, a signal quality for each of the mini zone scans is calculated at 156, such as in the manner as described above. At 158, an FHR waveform for each of the mini zone scans is determined by the FHR detector 110, which also may determine an average FHR at 160 from the FHR waveform. The average FHR may also be determined by the HRC detector 118.

At 162, the HRC detector 118 determines a coincidence between the average FHR for the mini zone scan and the reference FHR calculated at 152. The HRC detector 118 may also determine a stability of the FHR waveform at 164.

Starting at 166, exemplarily the TD selector 126 of FIG. 4, receives the calculated signal quality, FHR coincidence, and FHR waveform stability for each of the overlapping mini zone increments and identifies adjacent mini zones with maximum signal quality.

At 168, the TD selector verifies that the mini zones identified at 166 have FHR waveforms that are stable and have average FHR coincident to the reference FHR calculated at 152. In an embodiment, this is performed using a HRCx signal from the HRC detector 118. If the mini zones identified at 166 have a FHR waveform which is not stable and/or the average FHR is not coincident to the reference FHR, then the maternal artifact alarm 130 is generated at 170.

If the mini zones identified at 166 are verified at 168 as having a stable FHR waveform and a coincident average FHR, then at 172 the TD selector 126 verifies that the mini zones above or below an overlap of the identified mini zones have FHR waveform which is stable and the average FHR is not coincident to the reference FHR. If the FHR waveform of either mini zone above or below an overlap of the identified mini zones is stable and the average FHR is non-coincident with the reference FHR, then a maternal artifact alarm 130 is generated by the TD selector 126 at 170. Otherwise the process continues to 176 as described in further detail below.

The verifications at 168 and 172 are used to not only alarm an identified risk of maternal artifacts, but, if possible, narrow the scan range to avoid potential maternal artifacts. If the verification at 168 is false or the verification at 172 is true, resulting in a maternal artifact alarm at 170, then the ultrasound transducer is operated at 174 at a scan depth of the entire zone of sensitivity. The TD selector 126 products a TD selection signal (TDy) 128 indicative of the entire zone of sensitivity. If the verification at 168 is true or the verification at 172 is false, then at 176 the micro zone (e.g. 3 cm) overlapped by the mini zones (e.g. 6 cm) identified at 166 is selected as the location of the fetal heart and at 178 the ultrasound transducer is operated at a scan range of a macro zone (e.g. 9 cm) centered on the micro zone selected at 176. Referring back to FIG. 4, the ultrasound transducer 72 is operated in the manner at 178 by the TD selector 126 selecting a timing diagram selection signal 128 indicative of the macro zone centered on the selected micro zone. The timing diagram selection signal 128 is provided from the TD selector 126 to a TD scheduler 132 where the TD scheduler 132 provides a timing diagram code selection 134 to the digital logic 78 such that the digital logic 78 accesses the selected timing diagram from the computer readable medium 80 and operates the ultrasound transducer in accordance with the selected timing diagram. The TD scheduler 132 can provide the appropriate TD selection codes 134 in order to carry out the desired operation of the ultrasound transducer, exemplarily to provide the incremental scanning through each of the mini zones in order to carry out the maternal artifact detection, mitigation, and alarming features as disclosed above. The TD scheduler 132 may also receive user inputs from a user input device 136 such as to exemplarily initiate a new maternal artifact detection, migration, and alarm procedure, or to exemplarily edit timing diagrams stored at the computer readable medium 80.

In an non-limiting embodiment of exemplary timing diagrams as may be used in connection with embodiment as disclosed herein, the timing diagrams identify the timing of the TRANS signal 82 and the DETQ signal 84 provided by the digital logic as shown in FIG. 4. In embodiments, the CH signal 88 may be coincident with the DETQ signal 84. The table below provides timing information wherein time t(i) define the TRANS signal 82 and time r(i) define the DETQ signal 84 where odd numbered i values indicate signal starts and even numbered i values indicate the end of the signals. In the embodiments, x and y are the depth in centimeters that define the boundaries of the ultrasound depth range to be scanned.

| TRANS | | DETQ/CH | |
|---|---|---|---|
| t1 = 0 | t2 = 90 | r1 = 90 + 2 * x/0.154 | r2 = 2 * y/0.154 |
| t3 = t1 + 440 | t4 = t2 + 440 | r3 = r1 + 440 | r4 = r2 + 440 |
| t5 = t3 + 440 | t6 = t4 + 440 | r5 = r3 + 440 | r6 = r4 + 440 |
| t7 = t5 + 440 | t8 = t6 + 440 | r7 = r5 + 440 | r8 = r6 + 440 |

The fetal heart rate 112 from the FHR detector 110 is exemplarily provided to a graphical display 138 for visual presentation. In an alternative embodiment, the calculated fetal heart rate 112 is provided to a printer 140, such as, but not limited to a strip chart printer or a paper record of the calculated fetal heart rate. The maternal artifact alarm 130 and the signal quality alarm 116 are also provided to the graphical display 138, wherein if these alarms are initiated, a visual presentation of an alarm indication may be presented on the graphical display. In additional or alternative embodiments, the signal quality alarm 116 and the maternal artifact alarm 130 are provided to multiplexor 142 along with the fetal component signal 104. These signals are provided through an amplifier 144 and output through a speaker 146 such as to respectively produce audible alarms for maternal artifact detection, signal quality, as well as an audible presentation of the fetal heart activity.

The following is a non-limiting embodiment of an exemplary implementation of features and methods as disclosed herein. In this non-limiting embodiment, the micro zones are three centimeters deep, the mini zones are six centimeters deep, and the macro zones are nine centimeters deep. This description is presented with reference to the diagram of FIG. 6.

In order to detect a micro zone in which the fetal heart is located the fetal monitor scans through each of a plurality of mini zones: mini zone 200 (11-17 cm), mini zone 202 (14-20 cm), mini zone 204 (17-23 cm), mini zone 206 (20-26 cm), mini zone 208 (23-29 cm), and mini zone 210 (26-32 cm) on a zone by zone basis. The monitor evaluates the signal quality of the ultrasound signal for each mini zone, exemplarily by determining an energy of the signal. The monitor determines an FHR waveform for each mini zone and calculates an average FHR from the FHR waveform. The monitor calculates the average fetal heart rate across the entire ultrasound sensitivity zone (14-28 cm) and uses this as a reference FHR. In one embodiment, this reference FHR is calculated only at the start of the micro zone detection process, while in other embodiments, the reference FHR is calculated incrementally throughout the detection process, exemplarily at the beginning, middle, and end of the detection process. In a non-limiting embodiment, the process may take 90 seconds with reference FHR across the entire range calculated at 0, 40, and 80 seconds, respectively. Further in an embodiment, mini zone 200 is scanned at 10 seconds, mini zone 202 is scanned at 20 seconds, mini zone 204 is scanned at 30 seconds, mini zone 206 is scanned at 50 seconds, mini zone 208 is scanned at 60 seconds, and mini zone 210 is scanned at 70 seconds.

Figure 6:
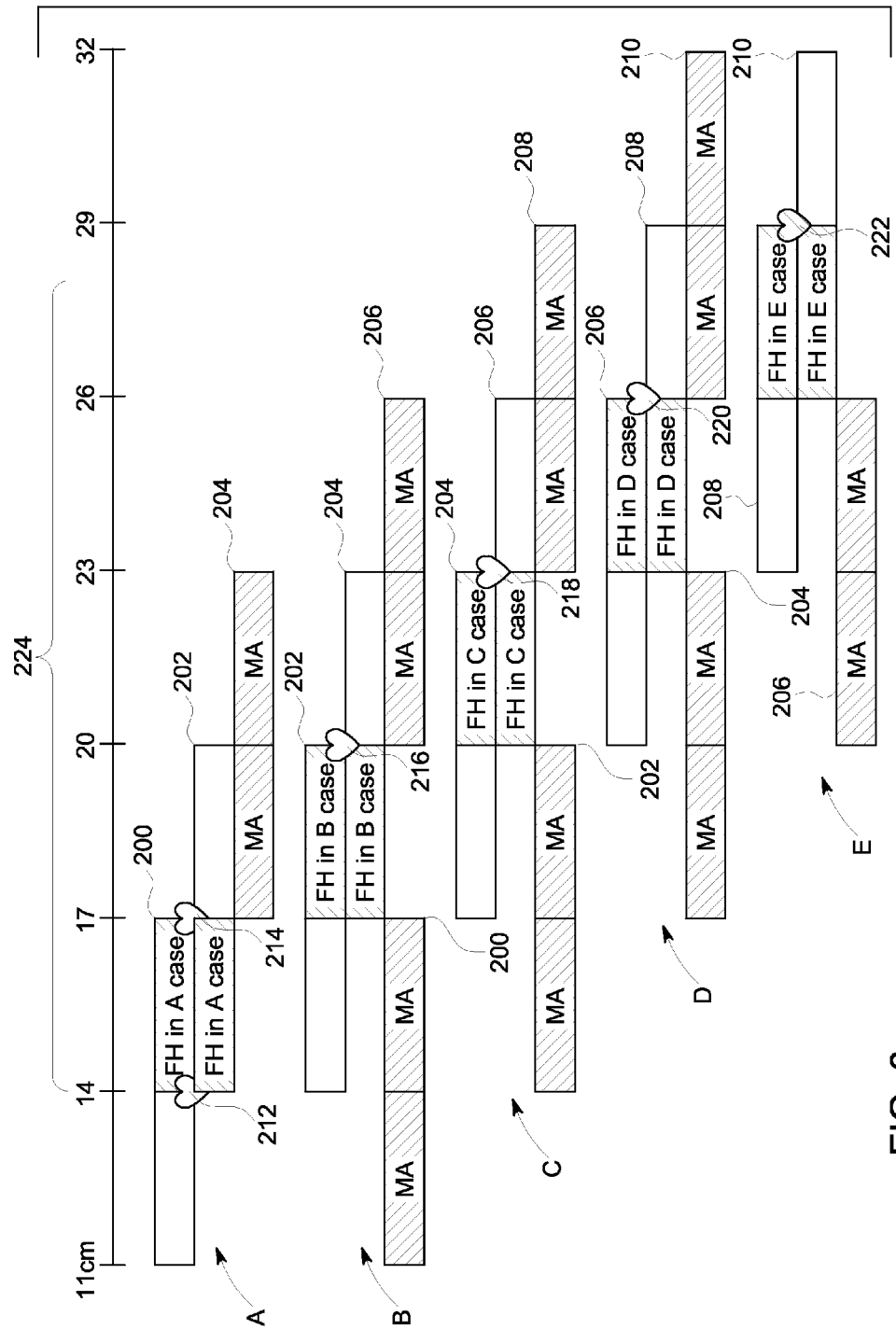
FIG. 6 diagrammatically depicts exemplary embodiments of scan depths associated with various timing diagrams.

The following example specifically refers to example B in FIG. 6 where exemplarily the ultrasound signals of the maximum signal quality were detected in mini zones 202 (14 cm-20 cm) and 204 (17 cm-23 cm). This means that the fetal heart signal is located in the micro zone overlapped by these two mini zones, exemplarily the micro zone between 17-20 cm. In the verification process, the monitor exemplarily verifies that the FHR waveforms in both mini zones 202 and 204 are stable (e.g. no pen lifts) and the average FHR calculated from each of the FHR waveforms is coincident to the reference FHR. In one embodiment as disclosed herein, the FHR is coincident if it is within 5% of the reference FHR. If this verification is true, then the monitor begins monitoring the fetal heart rate within the macro zone between 14 cm-23 cm as this macro zone is centered on the micro zone 17 cm-20 cm that contains the fetal heart. If these are not verified, then a maternal artifact alarm is generated and the monitor monitors fetal heart rate across the entire zone of sensitivity 224 (14 cm-28 cm).

In an embodiment, mini zones 200 and 206 are also verified as these are the mini zones adjacently above and below the two identified mini zones 202 and 204 that contain the fetal heart. In another manner of describing mini zones 200 and 206, mini zone 200 and 206 are the mini zones directly above and directly below the micro zone identified to contain the fetal heart. This verification checks if a maternal artifact is present in close proximity to the fetal heart. If either of the FHR waveforms in mini zone 200 (11 cm-17 cm) is stable but the average FHR of mini zone 200 is not coincident with the reference FHR or if the FHR waveform in mini zone 206 (20 cm-26 cm) is stable but the average FHR of the mini zone 206 is not coincident with the reference FHR, then a maternal artifact is present and in close proximity to the fetal heart. A maternal artifact alarm is generated and fetal heart rate is monitored in the entire zone of sensitivity 224 (14 cm-28 cm). Otherwise, no maternal artifact alarm is generated and the fetal heart rate is monitored in the macro zone 14 cm-23 cm.

FIG. 6 is described in further detail herein with respect to an exemplary embodiment of an algorithm implemented by the TD selector 126 (FIG. 4). In an exemplary embodiment, the TD selection algorithm includes:

Xmax1=maximum of (SQDx*HRCx) for ultrasound segments acquired at each mini zone.

Xmax2=maximum of (SQDx*HRCx) for the ultrasound segments acquired at each mini zone excluding the mini zone identified as Xmax1.

The timing diagram selection (TDY is selected according to the exemplary table provided below:

|  |  | Xmax2 | | | | | | |
| --- | --- | --- | --- | --- | --- | --- | --- | --- |
|  |  | 1117 | 1420 | 1723 | 2026 | 2329 | 2632 | no Xmax2 |
| Xmax1 | 1117 |  | A | AA | AA | AA | AA | A1 |
|  | 1420 | A |  | B | AB | AB | AB | A2 |
|  | 1723 | BC | B |  | C | BC | BC | B1 |
|  | 2026 | CD | CD | C |  | D | CD | C1 |
|  | 2329 | DE | DE | DE | D |  | E | D1 |
|  | 2632 | EE | EE | EE | EE | E |  | E1 |
|  | no Xmax1 |  |  |  |  |  |  | F |

Examples A-E in FIG. 6 corresponds to conditions A-E found in the table above. It is to be noted that condition F represents the case when the fetal heart signal is corrupted by the maternal artifacts within the two identified mini zones. While unlikely, it is possible that operation in condition F representing a scan across the entire sensitivity zone may mitigate this corruption. The other conditions in the table, namely AA, AB, BC, CD, DE, and EE cases identify multiple mini zones that provide heart rate signals of good quality (e.g. close to the reference fetal heart rate) but these mini zones do not overlap such that the fetal heart can be located within a micro zone. It is possible, although rare that echoes between the fetal heart and the umbilical cord may produce such a condition.

Conditions A1-E1 are exemplarily shown in FIG. 6 and represent a condition wherein the fetal heart falls precisely in the middle of a mini zone and therefore does not produce a second mini zone with a maximum signal quality. Looking at example A in FIG. 6, the A1 condition is shown at 212 and the A2 condition is shown at 214. Location 212 falls in the middle of mini zone 200 and therefore mini zone 200 would be the only mini zone to produce a maximum signal quality. Similarly, fetal heart location 214 falls in the middle of mini zone 202 and therefore the signal quality from mini zone 202 will be so much higher than that of mini zone 200 that the average FHR from mini zone 200 will not be stable. The FHR will not be coincident with the reference FHR, therefore only one maximum mini zone is identified. The B1 condition is represented at 216, the C1 condition is represented at 218, the D1 condition is represented at 220, and the E1 condition is represented at 222.

In most cases, as shown in examples A, B, C, D, and E depicted in FIG. 6, the fetal heart is located in a single micro zone that is common to two overlapping mini zones. Maternal artifacts, if any, are detected in mini zones adjacent to the fetal heart's micro zone. Embodiments as disclosed herein mitigate maternal artifact risk as it is unlikely that the maternal artifact is in the same micro zone as the fetal heart. So long as the maternal artifacts are at least in a micro zone adjacent to the fetal heart micro zone, embodiments are able to detect the maternal artifact based on the non-coincidence between stable heart rates (if any) calculated in the mini zones adjacent to the fetal heart micro zone as compared the reference fetal heart rate.

In order to reduce scan time one embodiment as disclosed herein does not detect maternal artifacts in a mini zone below the lowest fetal heart micro zone in the ultrasound sensitivity zone 224 such as shown in example A in FIG. 6 and the embodiment does not detect maternal artifacts above the deepest fetal heart micro zone within the ultrasound sensitivity zone 224 as shown in example E in FIG. 6.

The increase in ultrasound monitoring depth result in an increased risk of maternal artifacts within the deeper scan range. Embodiments as disclosed herein presents solutions that can tune the scan range in an effort to mitigate maternal artifact risk and also to identify conditions wherein risk of maternal artifacts exist and provide a warning of such condition.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method of monitoring a fetal heart rate, the method comprising:
   detecting, average fetal heart rate (FHR) with an ultrasound probe across an ultrasound depth zone of sensitivity as a reference FHR;
   scanning at least the ultrasound depth zone of sensitivity with the ultrasound probe in overlapping increments of a first depth;
   calculating a signal quality for each overlapping increment;
   identifying adjacent overlapping increments with a maximized signal quality;
   operating an ultrasound probe across an ultrasound depth increment of a second depth representing the adjacent overlapping increments to produce a returned ultrasound signal;
   determining FHR from the returned ultrasound signal.

2. The method of claim 1, wherein the ultrasound depth zone of sensitivity is between 14 centimeters and 28 centimeters from the ultrasound probe.

3. The method of claim 1, wherein the first depth is 6 centimeters in a direction away from the ultrasound probe and the second depth is 9 centimeters in a direction away from the ultrasound probe.

4. The method of claim 1 further comprising:
   determining an FHR waveform at each overlapping increment; and
   determining an FHR waveform stability at each overlapping increment.

5. The method of claim 4, further comprising:
   determining an average increment FHR for each overlapping increment from the FHR waveform at each overlapping increment; and
   determining a coincidence between the average increment FHR and the reference FHR across the ultrasound depth zone of sensitivity.

6. The method of claim 5, further comprising:
   verifying that the identified adjacent overlapping increments with the maximized signal quality have stable FHR waveforms and an average increment FHR is coincident to the detected reference FHR;
   wherein if the identified adjacent overlapping increments with the maximized signal quality have stable FHR waveforms and the average increment FHR is coincident to the detected reference FHR, then the ultrasound probe is operated across the ultrasound depth increment of the second depth, and
   if the identified adjacent overlapping increments with the maximized signal quality do not have a stable FHR waveform or the average increment FHR is not coincident to the detected reference FHR, then an alarm is produced indicating a possible maternal artifact.

7. The method of claim 6, further comprising:
   verifying that either of an increment adjacently above or an increment adjacently below the identified adjacent overlapping increments have a stable FHR waveform and the average increment FHR is coincident to the detected reference FHR;
   wherein if at least one of the adjacently above or adjacently below increments have a stable FHR waveform and average increment FHR which is not coincident to the detected reference FHR, then an alarm is produced indicating a possible maternal artifact; and
   wherein if the increments do not have stable FHR waveforms or the increments have average increment FHR coincident to the detected reference FHR, then the ultrasound probe is operated across the ultrasound depth increment of the second depth.

8. The method of claim 7, wherein if the alarm indicating a possible maternal artifact is produced, the ultrasound probe is operated across the ultrasound depth zone of sensitivity.

9. The method of claim further comprising:
   identifying an overlapped portion of the adjacent overlapping increments; and
   selecting, a timing diagram to operate the ultrasound transducer to produce an ultrasound signal based upon the selected ultrasound depth increment of a second depth representing the overlap of the adjacent overlapping, increments.

10. The method of claim 1, further comprising, updating the detected average FHR across the ultrasound depth zone of sensitivity.

11. A device for monitoring fetal heart rate, the device comprising:
    an ultrasound transducer operable to transmit ultrasound pulses over a zone of sensitivity and receive an ultrasound signal of reflected ultrasound pulses according to a timing diagram;
    a digital controller that operates the ultrasound transducer according to the timing diagram to scan the ultrasound depth zone of sensitivity in overlapping depth increments, the ultrasound transducer receiving the reflected ultrasound pulses from each over lapping depth increment;
    a fetal heart rate (FHR) detector operable to produce a reference FHR from across the zone of sensitivity, an FHR waveform for each of the overlapping depth increments of the zone of sensitivity, and calculate an average FHR from the FHR waveform;

a heart rate coincidence detector that compares the determined average FHR over an individual segment to a reference FHR calculated as the average FHR over the zone of sensitivity and produces a coincidence signal indicating a closeness between the average FHR and the reference FHR and a stability of the FHR waveform;

a signal quality detector that calculates a signal quality of the reflected ultrasound pulses of the ultrasound signal from each overlapping depth increment and produces a quality signal;

a timing diagram selector that receives the coincidence signal and the quality signal and selects adjacent overlapping increments with maximized quality signals and produces an indication of a maternal artifact alarm if the coincidence signals of the selected adjacent overlapping increments indicate no coincidence and produces an indication of a timing diagram associated with a combined scan depth of the selected adjacent overlapping increments for use by the digital controller in operation of the ultrasound transducer.

12. The device of claim 11, wherein the ultrasound transducer operates according to the selected timing diagram and FHR is determined from the received ultrasound signal independent of the indicated maternal artifact alarm.

13. The device of claim 12, further comprising a computer readable medium upon which a plurality of timing diagrams are stored, each timing diagram of the plurality being associated with an individual segment of the zone of sensitivity.

14. The device of claim 13, wherein the timing diagram defines at least a start time and an end time for a series of transmit tone signals and received tone signals.

15. A device for monitoring the heart rate of a fetus, the device comprising:

an ultrasound transducer operable to transmit an ultrasound signal and receive reflected ultrasounds signals from a plurality of ultrasound depths across an ultrasound depth zone of sensitivity;

a digital controller that operates the ultrasound transducer according to a timing diagram to scan the ultrasound depth zone of sensitivity in overlapping increments;

a signal quality detector that calculates a signal quality for each overlapping increment;

a fetal heart rate (FHR) detector that calculates a FHR waveform from each of the overlapping increments of a first depth size and calculates an average FHR from the FHR waveform; and a timing diagram selector that identifies adjacent overlapping increments with maximized signal quality and selects a timing diagram for use by the digital controller, wherein the timing diagram is associated with a combined scan depth of the identified adjacent overlapping increments;

wherein the digital controller operates the ultrasound transducer according to the selected timing diagram and the FHR detector calculates the FHR from the received reflected ultrasound signals produced according to the selected timing diagram.

16. The device of claim 15, further comprising:

a heart rate coincidence detector that receives the FHR waveform and average FHR for each of the overlapping increments from the FHR detector and determines a stability of the FHR waveform and determines a coincidence between the average FHR and a reference FHR calculated as an average FHR across the ultrasound depth zone of sensitivity;

wherein the timing diagram selector selects a timing diagram in part based upon the stability of the FHR waveform and the coincidence for each of the overlapping increments.

17. The device of claim 16, wherein if the identified adjacent overlapping increments with the maximized signal quality do not have a stable FHR waveform or the average FHR is not coincident to the reference FHR, the timing diagram selector products an alarm indicating a possible maternal artifact.

18. The device of claim 17, wherein if at least one of an increment adjacently above or adjacently below the identified adjacent overlapping increments with maximized signal quality have a stable FHR waveform and an average FHR which is not coincident to the reference FHR, the timing diagram selector products an alarm indicating a possible maternal artifact.

19. The device of claim 18, further comprising, an envelope detector that produces an envelope signal from the received reflected ultrasound signal and the signal quality detector receives the received reflected ultrasound signal and the FHR detector receives the envelope signal.

20. The device of claim 15, wherein the digital logic is operable to receive a selection of an ultrasound depth zone of sensitivity and at least one ultrasound depth zone of sensitivity corresponds to an ultrasound depth range between 3 centimeters and 17 centimeters and at least another ultrasound depth zone of sensitivity corresponds to an ultrasound depth range between 14 centimeters and 28 centimeters.

* * * * *